United States Patent
Liu et al.

(10) Patent No.: US 11,214,552 B2
(45) Date of Patent: Jan. 4, 2022

(54) PREPARATION METHOD FOR AZOXYSTROBIN AND INTERMEDIATE THEREOF

(71) Applicant: PURPANA (BEIJING) TECHNOLOGIES CO., LTD, Beijing (CN)

(72) Inventors: Binlong Liu, Beijing (CN); Ge Xu, Beijing (CN); Zhihui Wang, Beijing (CN)

(73) Assignee: PURPANA (BEIJING) TECHNOLOGIES CO., LTD, Beijing (CN)

( * ) Notice: Subject to any disclaimer, the term of this patent is extended or adjusted under 35 U.S.C. 154(b) by 0 days.

(21) Appl. No.: 17/040,894

(22) PCT Filed: May 30, 2018

(86) PCT No.: PCT/CN2018/089073
§ 371 (c)(1),
(2) Date: Sep. 23, 2020

(87) PCT Pub. No.: WO2019/178947
PCT Pub. Date: Sep. 26, 2019

(65) Prior Publication Data
US 2021/0009532 A1    Jan. 14, 2021

(30) Foreign Application Priority Data
Mar. 23, 2018    (CN) .......................... 201810246245.0

(51) Int. Cl.
*C07D 239/52*    (2006.01)
(52) U.S. Cl.
CPC ................... *C07D 239/52* (2013.01)
(58) Field of Classification Search
CPC .................................................. C07D 239/52
See application file for complete search history.

(56) References Cited

U.S. PATENT DOCUMENTS

2008/0214587 A1    9/2008    Whitton et al.

FOREIGN PATENT DOCUMENTS

| CN | 1219537 A | 6/1999 |
| CN | 101157657 A | 4/2008 |
| CN | 102190629 A | 9/2011 |
| CN | 103030598 A | 4/2013 |
| CN | 103467387 A | 12/2013 |
| CN | 104230819 A | 12/2014 |
| CN | 104230820 A | 12/2014 |
| CN | 104672146 A | 6/2015 |

(Continued)

OTHER PUBLICATIONS

English Translation from PCT/CN2018/089073 International Search Report dated Jan. 4, 2019 (4 pages).

*Primary Examiner* — Deepak R Rao
(74) *Attorney, Agent, or Firm* — Calfee Halter & Griswold LLP

(57) ABSTRACT

The present invention relates to the preparation field of azoxystrobin, and discloses a preparation method for a compound represented by formula (I). The method comprises the following steps: (1) a compound represented by formula (II) is hydrolyzed in a solvent under acidic conditions to obtain a compound represented by formula (III); and (2) the compound represented by formula (III) is reacted with a base and a methylating agent to obtain the compound represented by formula (I); in the formula, $R_3$ is hydrogen or $C_1$-$C_4$ alkyl, and $R_4$ is $C_1$-$C_4$ alkyl. The process for preparing azoxystrobin of the present invention not only successfully replaces trimethyl orthoformate and reduces the raw material cost, but also has high total reaction yield, and is suitable for industrial large-scale production. Experiments have proven that the yield of the prepared azoxystrobin can reach 95%.

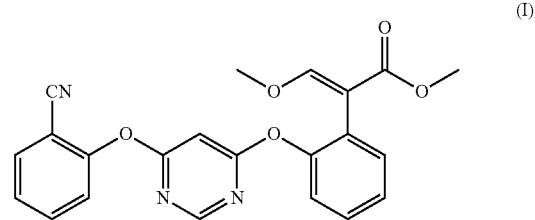

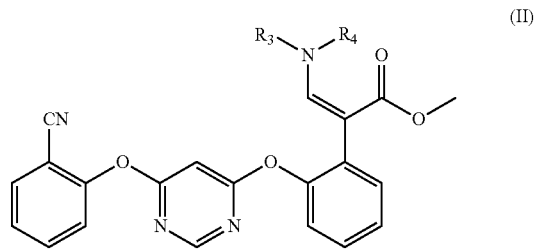

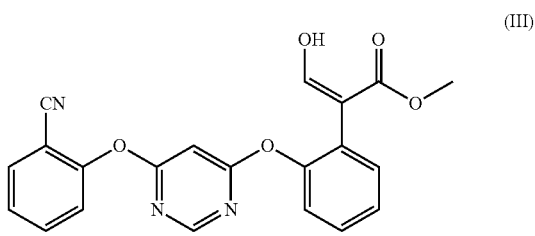

10 Claims, No Drawings

(56) References Cited

FOREIGN PATENT DOCUMENTS

| | | |
|---|---|---|
| CN | 104926736 A | 9/2015 |
| CN | 107235920 A | 10/2017 |
| CN | 107602480 A | 1/2018 |
| EP | 0592435 A1 | 4/1994 |
| WO | 0172719 A1 | 10/2001 |
| WO | 2008043977 A1 | 4/2008 |
| WO | 2013026391 A1 | 2/2013 |
| WO | 2017060917 A1 | 4/2017 |

PREPARATION METHOD FOR AZOXYSTROBIN AND INTERMEDIATE THEREOF

CROSS-REFERENCE TO RELATED APPLICATIONS

This application is the National Stage of International Application No. PCT/CN2018/089073, filed on May 30, 2018, which claims priority to Chinese Patent Application No. 201810246245.0 filed on Mar. 23, 2018, which are incorporated herein by reference in their entireties.

disclosed in the prior art EP0592435A1 and US 2008214587 A1. Generally, benzofuranone reacts with trimethyl orthoformate under the conditions of acetic anhydride to generate 3-methoxy methyl alkenyl-2-benzofuranone, then the 3-methoxy methyl alkenyl-2-benzofuranone and 4,6-dichloropyrimidine carry out ring opening etherification reaction under the conditions of sodium methoxide, then elimination reaction occurs under the conditions of sulfuric acid and the like to obtain (E)-3-methoxy-2-(2-(4-chloro-6-pyrimidine) oxyphenyl)-methyl acrylate, and finally etherified with salicylonitrile under the conditions of alkali and catalyst triethylene diamine to obtain azoxystrobin.

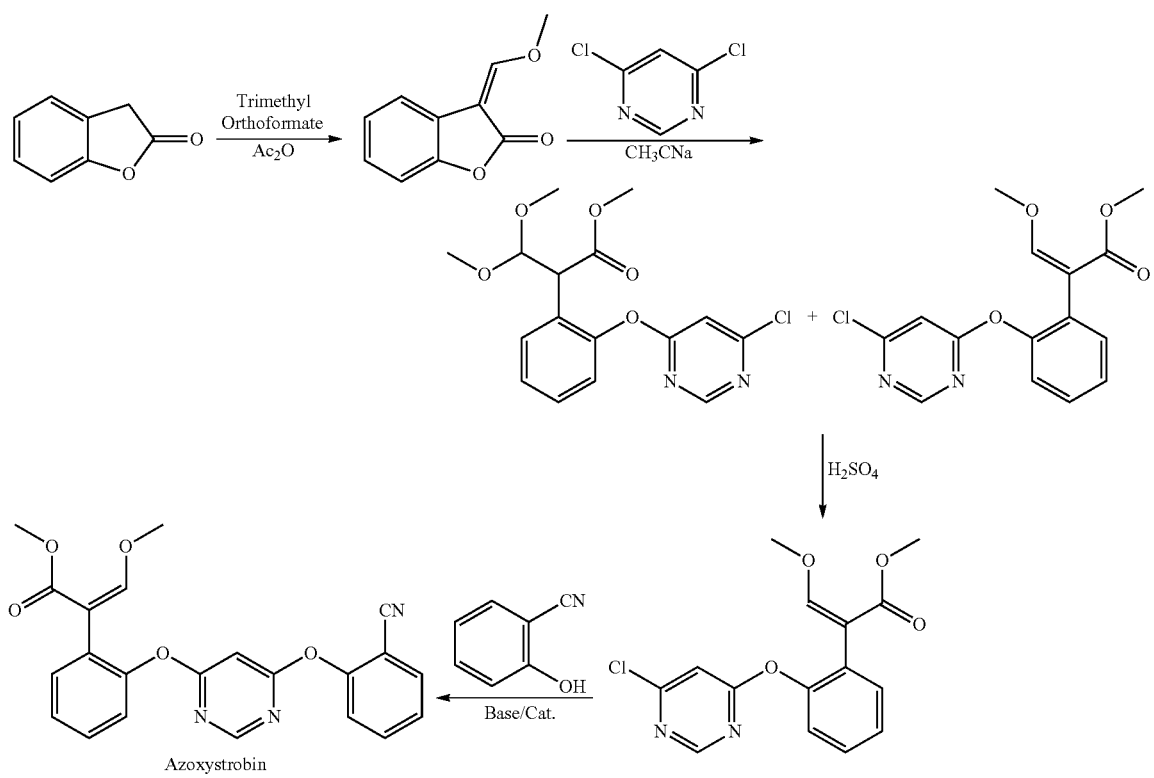

FIELD OF THE INVENTION

The present invention relates to the field of preparation of an agricultural fungicide azoxystrobin, in particular to a preparation method of azoxystrobin and intermediate thereof.

BACKGROUND OF THE INVENTION

Azoxystrobin is a strobilurin fungicide developed and commercialized by Zeneca (now Syngenta), and is an agricultural fungicide product with the largest global sales amount at present. Azoxystrobin is a high-efficiency, broad-spectrum and novel fungicide, which can prevent and treat almost all fungi, oomycetes, phycomycetes and other diseases. It is widely used in crops such as grains, rice, grapes, potatoes, and fruit trees.

At present, the technologies used in the industrial production of azoxystrobin basically refer to the technologies In the azoxystrobin preparation process, expensive trimethyl orthoformate is used in the synthesis of methoxy methyl alkenyl benzofuranone, and it reacts with acetic anhydride at high temperature (100-105° C.) for a long time, so that the cost is high. For example, CN1219537A discloses that the benzofuranone takes acetic anhydride as a solvent, and reacts with methyl orthoformate at 100-105° C. for 20 hours to prepare 3-methoxy-methyl alkenyl-2-benzofuranone. The reaction not only needs high temperature, but also has incomplete conversion of raw materials after 20 hours of reaction, so that the final product has poor properties, and high-quality azoxystrobin is difficult to obtain. CN101157657A discloses a method for constructing methoxy methyl alkenyl group by using titanium tetrachloride and trimethyl orthoformate. Although the reaction yield is high, the titanium tetrachloride needs equivalent consumption, the cost is high, and the wastes are more. In CN103030598A, N,N-dimethylformamide dimethyl acetal reacts with intermediate 2-(2-(6-(2-cyanophenoxy) pyrimidine-4-oxy) phenyl) methyl acetate at a high temperature to prepare intermediate 2-(2-(6-(2-cyanophenoxy) pyrimidine- 4-oxy) phenyl)-3-dimethylamino acrylate methyl ester, which is directly hydrolyzed in hydrochloric acid aqueous solution and then methylated to prepare azoxystrobin.

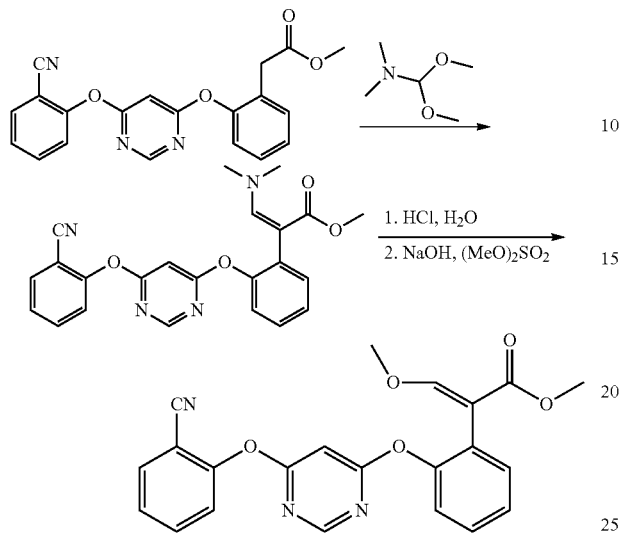

The method has the problems that there are many side reactions when preparing the intermediate 2-(2-(6-(2-cyanophenoxy) pyrimidine-4-oxy) phenyl) methyl acetate, resulting the yield is lower, in addition, the temperature for the reaction of N,N-dimethylformamide dimethyl acetal and the intermediate 2-(2-(6-(2-cyanophenoxy) pyrimidine-4-oxy) phenyl) methyl acetate is high, the inevitable generation of partial tar can cause the dark color of the final product azoxystrobin. In addition, the price of the N,N-dimethylformamide dimethyl acetal is high, the large-scale industrial production is not facilitated, and the hydrolysis method of the intermediate 2-(2-(6-(2-cyanophenoxy) pyrimidine-4-oxy) phenyl)-3-dimethylaminoacrylate methyl ester is hydrolyzed in hydrochloric acid water directly, has the defects of difficult stirring, incomplete reaction and the like, and leads to low total yield of azoxystrobin.

In conclusion, the existing methods have the defects of low total reaction yield, high raw material cost and the like when preparing azoxystrobin.

SUMMARY OF THE INVENTION

The present invention aims to overcome the problems of low total reaction yield, high raw material cost and the like in the preparation of azoxystrobin existing in the prior art, and to provide a preparation method of azoxystrobin and intermediate thereof.

In order to achieve the above object, one aspect of the present invention provides a method for preparing the compound represented by formula (II), which is performed in either of the following two ways:

(1) Reacting the compound represented by formula (IV) with the compound represented by formula (V) in which $Z_1$ is 2-cyanophenoxy group and $Z_2$ is halogen, in an organic solvent in the presence of sodium methoxide or potassium methoxide and catalyst;

(2) Reacting the compound represented by formula (IV) with the compound represented by formula (V) in the presence of sodium methoxide or potassium methoxide and catalyst, and then reacting with 2-cyanophenol in the presence of alkali and catalyst. In formula (V), both $Z_1$ and $Z_2$ are halogen;

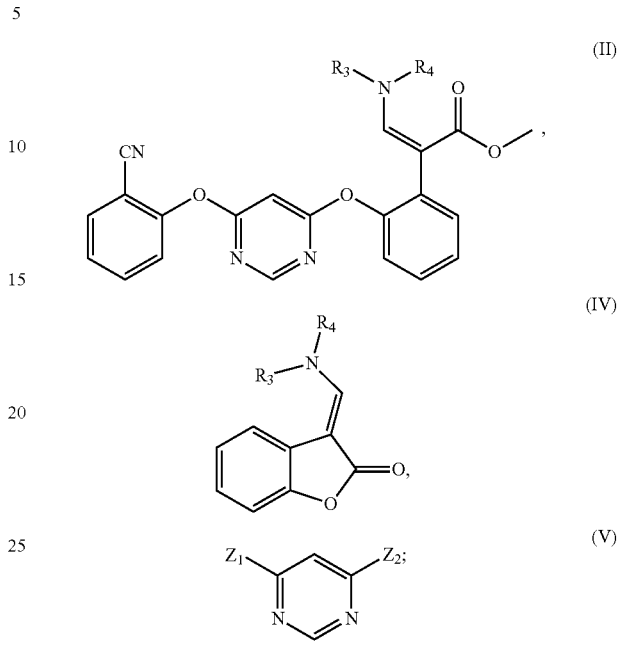

In the formula, $R_4$ is $C_1$-$C_4$ alkyl, and $R_3$ is hydrogen or $C_1$-$C_4$ alkyl.

In a second aspect, the present invention provides a process for preparing the compound represented by formula (I), which process comprises the steps of:

(1) Preparing the compound represented by formula (II) according to the method described above;

(2) Under acidic conditions, carrying out hydrolysis reaction on the compound represented by formula (II) in an organic solvent to obtain the compound represented by formula (III);

(3) Reacting the compound represented by formula (III) with alkali and methylating agent to prepare the compound represented by formula (I);

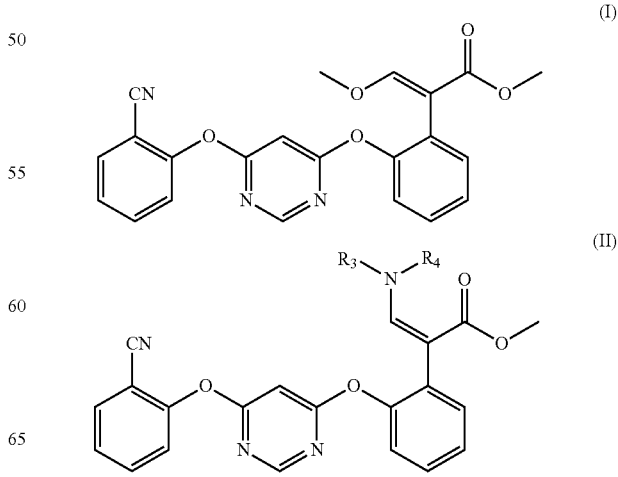

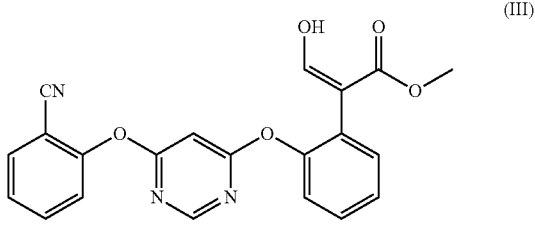

(III)

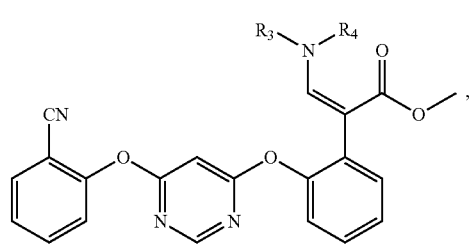

(II)

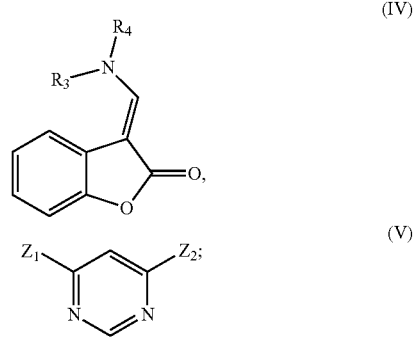

(IV)

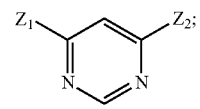

(V)

In the formula, $R_3$ is hydrogen or $C_1$-$C_4$ alkyl, and $R_4$ is $C_1$-$C_4$ alkyl.

In the present invention, azoxystrobin refers to the compound represented by formula (I), and the azoxystrobin intermediate refers to the compound represented by formula (II).

Through the technical scheme, in the present invention, the prepared azoxystrobin intermediate (the compound represented by formula (II)) is used as the starting raw material for preparing azoxystrobin (the compound represented by formula (I)), so that trimethyl orthoformate is successfully replaced, the raw material cost is reduced, and the total reaction yield of azoxystrobin is greatly improved, which is suitable for industrialized large-scale production. Experiments have proved that the yield of azoxystrobin can reach 95%.

DETAILED DESCRIPTION OF THE EMBODIMENTS

The endpoints of the ranges and any values disclosed herein are not limited to the precise range or value, and these ranges or values should be understood to encompass values close to these ranges or values. For numerical ranges, each range between its endpoints and individual point values, and each individual point value can be combined with each other to give one or more new numerical ranges, and such numerical ranges should be considered as specifically disclosed herein.

The following describes the embodiments of the present invention in detail. It should be understood that the detailed description and specific examples, while indicating the preferred embodiment of the invention, are given by way of illustration and explanation only, not limitation.

The present invention provides a method for preparing the compound represented by formula (II), which is operated according to either of the following two ways:

(1) Reacting the compound represented by formula (IV) with the compound represented by formula (V) in which $Z_1$ is 2-cyanophenoxy group and $Z_2$ is halogen, in an organic solvent in the presence of sodium methoxide or potassium methoxide and catalyst;

(2) Reacting the compound represented by formula (IV) with the compound represented by formula (V) in the presence of sodium methoxide or potassium methoxide and catalyst, and then reacting with 2-cyanophenol in the presence of alkali and catalyst. In formula (V), both $Z_1$ and $Z_2$ are halogen;

In the formula, $R_4$ is $C_1$-$C_4$ alkyl, and $R_3$ is hydrogen or $C_1$-$C_4$ alkyl.

In the present invention, the compound represented by formula (IV) replaces the process steps of generating the 3-methoxy methyl alkenyl-2-benzofuranone by reacting benzofuranone with trimethyl orthoformate under the conditions of acetic anhydride in the prior art, so that the production process is simplified, the reaction yield of azoxystrobin intermediate is improved under the action of catalyst of triethylene diamine type by using sodium methoxide or potassium methoxide, the production cost of azoxystrobin intermediate is reduced, and the production cost of azoxystrobin raw materials is reduced.

In the present invention, based on 1.00 molar equivalent of the compound represented by formula (IV), the compound represented by formula (V) is used in an amount of 0.6 to 3.0 molar equivalents, for example, 0.6 molar equivalent, 0.8 molar equivalent, 1.0 molar equivalent, 1.2 molar equivalents, 1.5 molar equivalents, 1.8 molar equivalents, 2 molar equivalents, 2.2 molar equivalents, 2.5 molar equivalents, 2.8 molar equivalents, 3.0 molar equivalents and any value in the range formed by any two of these points, preferably 0.8 to 1.8 molar equivalents; the sodium methoxide or potassium methoxide is used in an amount of 0.6 to 3.0 molar equivalents, for example, 0.6 molar equivalent, 0.8 molar equivalent, 1.0 molar equivalent, 1.2 molar equivalents, 1.5 molar equivalents, 1.8 molar equivalents, 2 molar equivalents, 2.2 molar equivalents. 2.5 molar equivalents, 2.8 molar equivalents, 3.0 molar equivalents and any value in the range formed by any two of these points, preferably 0.8 to 1.8 molar equivalents; the 2-cyanophenol is used in an amount of 0.6 to 3.0 molar equivalents, for example, 0.6 molar equivalent, 0.8 molar equivalent, 1.0 molar equivalent, 1.2 molar equivalents, 1.5 molar equivalents, 1.8 molar equivalents, 2 molar equivalents, 2.2 molar equivalents, 2.5 molar equivalents, 2.8 molar equivalents, 3.0 molar equivalents and any value in the range formed by any two of these points, preferably 0.8 to 1.8 molar equivalents; the alkali is used in an amount of 0.6 to 3.0 molar equivalents, for example, 0.6 molar equivalent, 0.8 molar equivalent, 1.0 molar equivalent, 1.2 molar equivalents, 1.5 molar equivalents, 1.8 molar equivalents, 2 molar equivalents, 2.2 molar equivalents, 2.5 molar equivalents, 2.8 molar equivalents, 3.0 molar equivalents and any value in the range formed by any two of these points, preferably 0.8 to 1.8 molar equivalents; the catalyst is used in an amount of 0.001 to 0.03 molar equivalent, for example. 0.001 molar equivalent, 0.002 molar equivalent, 0.005 molar equivalent, 0.008 molar equivalent, 0.01 molar equivalent, 0.012 molar equivalent, 0.015 molar equivalent, 0.018 molar equivalent, 0.02 molar equivalent, 0.022 molar equivalent, 0.025 molar equivalent, 0.028 molar equivalent, 0.03 molar equivalent and any value in the range formed by any two of these points, preferably 0.002 to 0.02 molar equivalent.

According to the present invention, in order to facilitate the production of the compound represented by formula (II), the reaction of the compound represented by formula (IV) with the compound represented by formula (V) is carried out in the step (2) at a temperature of −20° C. to 30° C.

Preferably, in the formula, $R_4$ is $C_1$-$C_4$ straight-chain alkyl, and $R_3$ is hydrogen or $C_1$-$C_4$ straight-chain alkyl. More preferably, in the formula, $R_4$ is methyl or ethyl; $R_3$ is hydrogen, methyl or ethyl.

Preferably, the halogen is fluorine, chlorine, bromine or iodine. More preferably, the halogen is chlorine or bromine.

In the present invention, the catalyst may be a catalyst of triethylene diamine type. Preferably, the catalyst is triethylene diamine and/or methyl triethylene diamine, so that the reaction yield can be greatly improved.

In the present invention, the organic solvent is various conventional solvents in the art, and is selected from at least one of toluene, xylene, methanol, ethanol, acetonitrile, ethyl acetate, butyl acetate, dichloromethane, N,N-dimethylformamide, and tetrahydrofuran. Preferably, the organic solvent is selected from at least one of toluene, methanol, ethanol, acetonitrile, butyl acetate, dichloromethane, and N,N-dimethylformamide.

In the present invention, the alkali may be various conventional alkalis in the art, and is selected from at least one of sodium hydroxide, potassium hydroxide, sodium carbonate, and potassium carbonate.

The present invention also provides a method for preparing the compound represented by formula (I), which comprises the following steps:

(1) Preparing the compound represented by formula (II) according to the method described above;

(2) Under acidic conditions, carrying out hydrolysis reaction on the compound represented by formula (II) in an organic solvent to obtain the compound represented by formula (III);

(3) Reacting the compound represented by formula (III) with alkali and methylating agent to prepare the compound represented by formula (I);

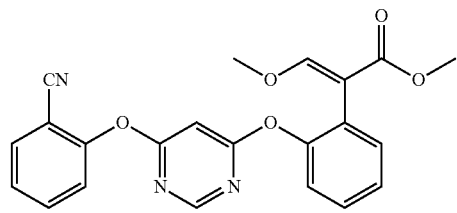

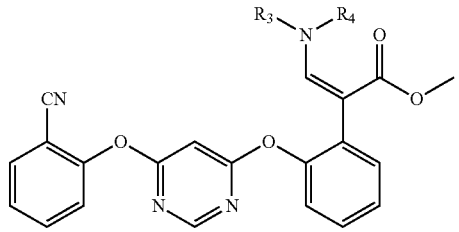

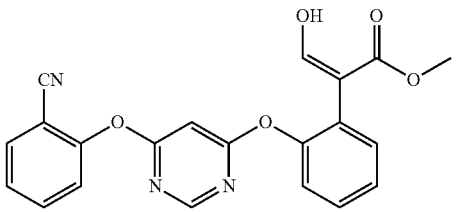

In the formula, $R_3$ is hydrogen or $C_1$-$C_4$ alkyl, and $R_4$ is $C_1$-$C_4$ alkyl.

In the present invention, the prepared azoxystrobin intermediate (the compound represented by formula (II)) is used as the starting raw material for preparing azoxystrobin (the compound represented by formula (I)), so that the cost is low, and the total reaction yield of azoxystrobin is greatly improved.

In the present invention, based on 1.00 molar equivalent of the compound represented by formula (II), the organic solvent is used in an amount of 0.6 to 3.0 molar equivalents, preferably 0.8 to 1.8 molar equivalents, the acidic conditions are adjusted by acids, the acid is used in an amount of 0.3 to 3.0 molar equivalents, preferably 0.5 to 1.5 molar equivalents, the alkali is used in an amount of 0.6 to 3.0 molar equivalents, preferably 0.8 to 1.8 molar equivalents, and the methylating agent is used in an amount of 1.0 to 5.0 molar equivalents, preferably 1.0 to 2.0 molar equivalents.

In the present invention, in order to facilitate the hydrolysis reaction of the intermediate of azoxystrobin, the hydrolysis reaction temperature in the step (1) is (−10° C.) to (100° C.).

Preferably, in the formula, $R_3$ is hydrogen or $C_1$-$C_4$ straight-chain alkyl, and $R_4$ is $C_1$-$C_4$ straight-chain alkyl. More preferably, $R_3$ is hydrogen, methyl or ethyl and $R_4$ is methyl or ethyl.

In the present invention, the acidic conditions are adjusted by acids, which may be various conventional acids in the art. For example, the acid may be selected from at least one of sulfuric acid, hydrochloric acid, phosphoric acid, methanesulfonic acid, formic acid, acetic acid, and trifluoroacetic acid. Preferably, the acid is at least one of trifluoroacetic acid, formic acid, hydrochloric acid and sulfuric acid, and more preferably formic acid, sulfuric acid and trifluoroacetic acid, so that the conversion rate of the reaction in the step is greatly improved.

In the present invention, the organic solvent is various conventional solvents in the art. For example, the organic solvent may be selected from at least one of toluene, xylene, methanol, ethanol, acetonitrile, ethyl acetate, butyl acetate, dichloromethane, N,N-dimethylformamide, and tetrahydrofuran. Preferably, the organic solvent is selected from at least one of toluene, methanol, ethanol, acetonitrile, butyl acetate, dichloromethane and N,N-dimethylformamide, and more preferably methanol, a mixed solvent of methanol and toluene, and a mixed solvent of acetonitrile and toluene, so that the conversion rate and yield of the reaction are greatly improved.

In the present invention, the alkali may be various conventional alkalis in the art, and is selected from at least one of sodium hydroxide, potassium hydroxide, sodium carbonate, and potassium carbonate.

In the present invention, the methylating agent may be various conventional methylating agents in the art. For example, the methylating agent may be selected from at least one of dimethyl sulfate, dimethyl carbonate, methyl chloride, methyl bromide and methyl iodide. Preferably, the methylating agent is selected from dimethyl sulfate and/or dimethyl carbonate.

The present invention will be described in detail below by way of examples. In the following embodiments:

The amounts of reactants and products were determined by liquid chromatography (Agilent HPLC 1260).

The conversion rate and yield of the reaction were calculated by the following formulas:

Conversion rate=(feed molar amount-residual feed molar amount in product)/feed molar amount×100%.

Yield=actual molar amount of target product/theoretical molar amount of target product×100%.

In the case where no particular description is given, commercially available products are used as the starting materials.

Example 1

Preparation of 2-(2-(6-chloropyrimidine-4-oxy) phenyl)-3-dimethylamino acrylate methyl ester (i.e., the compound of general formula (II) in which $Z_1$ is chlorine, $R_3$ and $R_4$ are methyl) 19.5 g of dimethylaminomethylbenzofuranone (namely, the compound with methyl $R_3$ and $R_4$ in formula IV) and 150 mL of toluene are added into a four-neck flask with mechanical stirrer, thermometer and condenser, 5.5 g of solid sodium methoxide is added, the mixture is stirred and reacted for 3 hours at room temperature, the temperature is reduced to −15° C., then 0.1 g of triethylene diamine is added, 4, 6-dichloropyrimidine is added at the same time, the mixture is stirred and reacted for 5 hours, then the mixture is heated to the room temperature, washed with water and layered, the solid obtained by concentrating the organic phase is 2-(2-(6-chloropyrimidine-4-oxy) phenyl)-3-dimethylamino acrylate methyl ester, and the next step of reaction is directly carried out without separation. The yield of 2-(2-(6-chloropyrimidine-4-oxy) phenyl)-3-dimethylamino acrylate methyl ester was measured to be 97%.

Example 2

Preparation of 2-(2-(6-(2-cyanophenoxy) pyrimidine-4-oxy) phenyl)-3-dimethylamino acrylate methyl ester (i.e., the compound of formula (II) in which $Z_1$ is 2-cyanophenyl, $R_3$ and $R_4$ are methyl)

34 g of 2-(2-(6-chloropyrimidine-4-oxy) phenyl)-3-dimethylamino acrylate methyl ester obtained in example 1, 12.0 g of salicylonitrile and 100 mL of N,N-dimethylformamide are added into a four-neck flask with mechanical stirrer, thermometer and condenser, 15.5 g of potassium carbonate is added, 0.1 g of triethylene diamine is added, the temperature is raised to 80° C., stirring reaction is carried out for 3 hours, then the solvent N,N-dimethylformamide is evaporated under reduced pressure, toluene is added for dissolution, the mixture is washed with water and layered, the solid obtained by concentrating the organic phase is 2-(2-(6-(2-cyanophenoxy) pyrimidine-4-oxy) phenyl)-3-dimethylamino acrylate methyl ester. The yield of 2-(2-(6-(2-cyanophenoxy) pyrimidine-4-oxy) phenyl)-3-dimethylamino acrylate methyl ester was measured to be 97%. $^1$H NMR DMSO-$d_6$ (δ, ppm): 3.62 (S, 3H), 4.02 (S, 6H), 6.75 (S, 2H), 7.22 (d, 1H), 7.26-7.43 (m, 5H) 7.66 (t, 1H), 7.73 (d, 1H), 8.38 (s, 1H).

Example 3

Preparation of 2-(2-(6-(2-cyanophenoxy) pyrimidine-4-oxy) phenyl)-3-dimethylamino acrylate methyl ester (i.e., the compound of formula (II) in which $Z_1$ is 2-cyanophenyl, $R_3$ and $R_4$ are methyl) 19.5 g of dimethylaminomethylbenzofuranone (namely, the compound with methyl $R_3$ and $R_4$ in formula IV) and 150 mL of toluene are added into a four-neck flask with mechanical stirrer, thermometer and condenser, 5.5 g of solid sodium methoxide is added, the mixture is stirred and reacted for 3 hours at room temperature, the temperature is reduced to −15° C., then 0.1 g of triethylene diamine is added, 4-(2-cyanophenoxy)-6-chloropyrimidine is added at the same time, the mixture is stirred and reacted for 5 hours, then the mixture is heated to room temperature, washed with water and layered, the solid obtained by concentrating the organic phase is 2-(2-(6-(2-cyanophenoxy) pyrimidine-4-oxy) phenyl)-3-dimethylamino acrylate methyl ester. The yield of 2-(2-(6-(2-cyanophenoxy) pyrimidine-4-oxy) phenyl)-3-dimethylamino acrylate methyl ester was measured to be 97%.

Example 4

Preparation of azoxystrobin

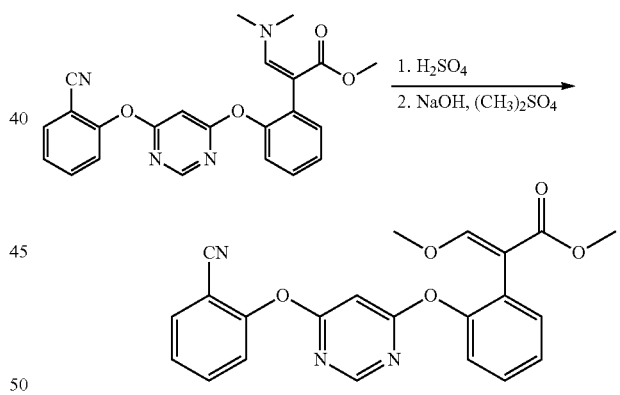

2-(2-(6-(2-cyanophenoxy) pyrimidine-4-oxy) phenyl)-3-dimethylamino acrylate methyl ester obtained in example 3 was put into methanol, 109 g of 18% aqueous solution of sulfuric acid was added dropwise at 25° C., the reaction was stirred at room temperature for 3 hours, then methanol was evaporated under reduced pressure, butyl acetate was added for extraction, the mixture was allowed to stand for layering, the aqueous layer was separated, the mixture was washed once with water, 40 g of aqueous solution of 20% sodium hydroxide was added, 15.2 g of dimethyl sulfate was added dropwise, the mixture was stirred at room temperature for 3 hours, the aqueous layer was separated by standing after the reaction was completed, and the organic phase was concentrated to obtain 38.5 g of azoxystrobin. The quantitative yield of the four-step reaction of azoxystrobin was measured to be 9.5%. $^1$NMR DMSO-$d_6$ (δ, ppm): 3.62 (S, 3H), 3.72

(S, 3H), 6.42 (S, 2H), 7.22 (d, 1H), 7.26-7.43 (m, 5H) 7.66 (t, 1H), 7.73 (d, 1H), 8.4 (s, 1H).

The preferred embodiments of the present invention have been described above in detail, but the present invention is not limited thereto. Within the scope of the technical idea of the present invention, various simple modifications can be made to the technical solution of the present invention, including various technical features being combined in any other suitable way, and these simple modifications and combinations should also be regarded as the disclosure of the present invention, and all fall within the scope of the present invention.

What is claimed is:

1. A method for preparing the compound represented by formula (II), characterized by operating in either of the following two ways:
    (1) reacting a compound represented by formula (IV) with a compound represented by formula (V) in which $Z_1$ is 2-cyanophenoxy group and $Z_2$ is halogen, in an organic solvent in the presence of sodium methoxide or potassium methoxide and catalyst;
    (2) reacting a compound represented by formula (IV) with a compound represented by formula (V) in the presence of sodium methoxide or potassium methoxide and catalyst, and then reacting with 2-cyanophenol in the presence of alkali and catalyst, in formula (V), both $Z_1$ and $Z_2$ are halogen;

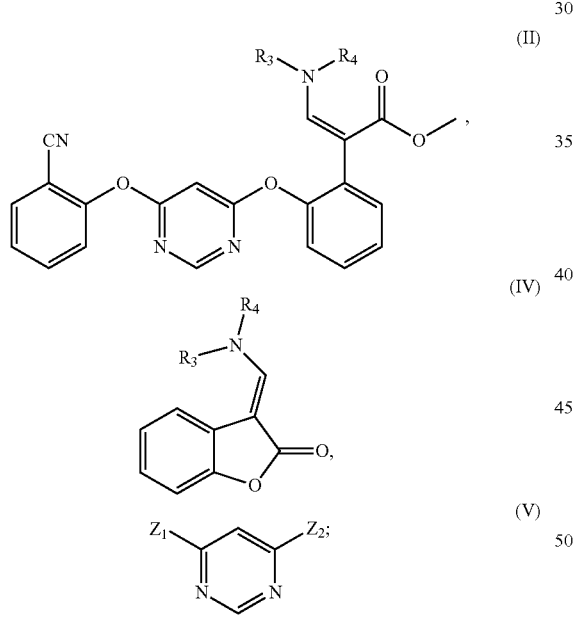

wherein $R_4$ is $C_1$-$C_4$ alkyl, and $R_3$ is hydrogen or $C_1$-$C_4$ alkyl.

2. The method according to claim 1, characterized in that, based on 1 molar equivalent of the compound represented by formula (IV),
    the compound represented by formula (V) is used in an amount of 0.6 to 3 molar equivalents;
    the sodium methoxide or potassium methoxide is used in an amount of 0.6 to 3 molar equivalents;
    the 2-cyanophenol is used in an amount of 0.6 to 3 molar equivalents;
    the alkali is used in an amount of 0.6 to 3 molar equivalents;
    the catalyst is used in an amount of 0.001 to 0.03 molar equivalent.

3. The method according to claim 1, wherein the reaction of the compound represented by formula (IV) with the compound represented by formula (V) is first carried out at a temperature of (−20° C.) to (30° C.) in the second way.

4. The method according to claim 1, wherein in the formula, $R_4$ is $C_1$-$C_4$ straight-chain alkyl, $R_3$ is hydrogen or $C_1$-$C_4$ straight-chain alkyl, and the halogen is fluorine, chlorine, bromine or iodine.

5. The method according to claim 1, wherein the catalyst is triethylene diamine and/or methyl triethylene diamine; the organic solvent is at least one selected from toluene, xylene, methanol, ethanol, acetonitrile, ethyl acetate, butyl acetate, dichloromethane, N,N-dimethylformamide and tetrahydrofuran; the alkali is at least one selected from sodium hydroxide, potassium hydroxide, sodium carbonate and potassium carbonate.

6. A method for preparing a compound represented by formula (I), characterized in that, the method comprises the following steps:
    (1) preparing a compound represented by formula (II) according to the method of claim 1;
    (2) under acidic conditions, carrying out hydrolysis reaction on the compound represented by formula (II) in an organic solvent to obtain a compound represented by formula (III);
    (3) reacting the compound represented by formula (III) with alkali and methylating agent to prepare the compound represented by formula (I);

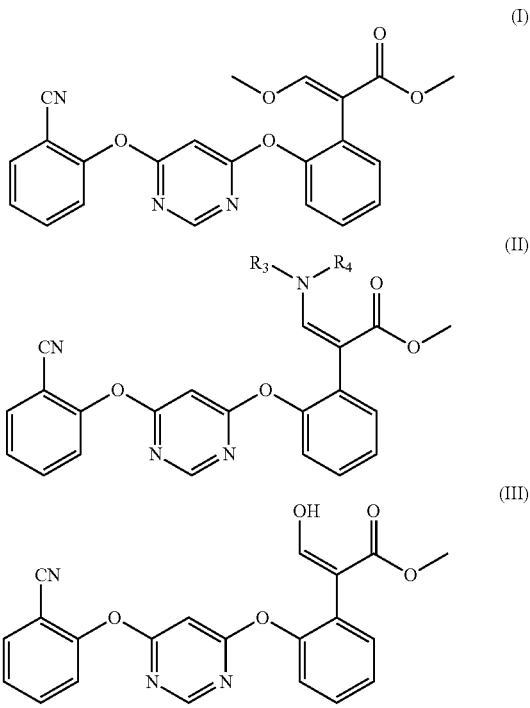

wherein $R_3$ is hydrogen or $C_1$-$C_4$ alkyl, and $R_4$ is $C_1$-$C_4$ alkyl.

7. The method according to claim 6, wherein based on 1 molar equivalent of the compound represented by formula (II),
    the organic solvent is used in an amount of 0.6 to 3 molar equivalents;

the acidic conditions are adjusted by acids, and the acid is used in an amount of 0.3 to 3 molar equivalents;
the alkali is used in an amount of 0.6 to 3 molar equivalents;
the methylating agent is used in an amount of 1 to 5 molar equivalents.

8. The method according to claim 6, characterized in that, the hydrolysis reaction temperature in the step (1) is (−10° C.) to (100° C.).

9. The method according to claim 6, wherein in the formula, $R_3$ is hydrogen or $C_1$-$C_4$ straight-chain alkyl, and $R_4$ is $C_1$-$C_4$ straight-chain alkyl.

10. The method according to claim 6, wherein the acidic conditions are adjusted by acids selected from at least one of sulfuric acid, hydrochloric acid, phosphoric acid, methanesulfonic acid, formic acid, acetic acid, and trifluoroacetic acid; the organic solvent is selected from at least one of toluene, xylene, methanol, ethanol, acetonitrile, ethyl acetate, butyl acetate, dichloromethane, N,N-dimethylformamide and tetrahydrofuran; the alkali is selected from at least one of sodium hydroxide, potassium hydroxide, sodium carbonate and potassium carbonate; the methylating agent is selected from at least one of dimethyl sulfate, dimethyl carbonate, methyl chloride, methyl bromide and methyl iodide.

* * * * *